US006611412B1

United States Patent
Reichwein

(10) Patent No.: US 6,611,412 B1
(45) Date of Patent: Aug. 26, 2003

(54) APPARATUS AND METHOD FOR MINIMIZING ELECTROMAGNETIC EMISSIONS OF TECHNICAL EMITTERS

(76) Inventor: Dietrich Reichwein, Bergstrasse 6 Top 26, Zell am See (AT), A-5700

( * ) Notice: Subject to any disclaimer, the term of this patent is extended or adjusted under 35 U.S.C. 154(b) by 60 days.

(21) Appl. No.: 09/830,604

(22) PCT Filed: Oct. 18, 2000

(86) PCT No.: PCT/EP00/10325

§ 371 (c)(1),
(2), (4) Date: Apr. 30, 2001

(87) PCT Pub. No.: WO01/39567

PCT Pub. Date: May 31, 2001

(30) Foreign Application Priority Data

Nov. 19, 1999 (DE) .......................................... 199 55 974
Feb. 10, 2000 (DE) .......................................... 100 05 905

(51) Int. Cl.$^7$ ................................................ A43B 5/04
(52) U.S. Cl. ..................................... 361/118; 250/515.1
(58) Field of Search ................................. 361/110, 111, 361/112, 113, 118; 250/505.1, 515.1

(56) References Cited

U.S. PATENT DOCUMENTS

| 685,957 A | 11/1901 | Tesla | |
| 6,249,006 B1 | 6/2001 | Sakiyama | 250/505.1 |

FOREIGN PATENT DOCUMENTS

| CH | 669733 | 4/1989 | A61N/1/16 |
| DE | 3938238 | 5/1991 | H01P/1/26 |
| DE | 19850238 | 5/2000 | A61N/1/16 |
| EP | 0 880 311 A1 | 11/1998 | H05K/9/00 |
| WO | WO 00/74461 A1 | 12/2000 | H05K/9/00 |

*Primary Examiner*—Edward H. Tso
(74) *Attorney, Agent, or Firm*—Brinks Hofer Gilson & Lione

(57) ABSTRACT

The present application concerns an apparatus and a method for minimizing electromagnetic emissions of technical emitters. Such methods and apparatuses are needed to minimize the potential vortex portions of electromagnetic alternating fields emitted by technical devices.

25 Claims, 5 Drawing Sheets

APPARATUS AND METHOD FOR MINIMIZING ELECTROMAGNETIC EMISSIONS OF TECHNICAL EMITTERS

BACKGROUND OF THE INVENTION

The invention described herein concerns an apparatus and a method for minimizing electromagnetic emissions of technical emitters, i.e., for minimizing the potential vortex portions of electromagnetic alternating fields caused by technical devices. It has been scientifically demonstrated in extensive studies that the alternating magnetic field, contrary to previous assumptions, not only acts by means of induction but through the formation and density of ring and potential vortex systems (K. Meyl, "Elektromagnetische Unverträglichkeit, Ursachen, Phänomene und naturwissenschaftliche Konsequenzen. Umdruck zur Vorlesung" [Electromagnetic Incompatibility, Causes, Phenomena and Scientific Consequences, Reprint for the Lecture], ISBN 3-9802-642-8-3 and ISBN 3-9802542-9-1, and K. Meyl, "Potentialwirbel" [Potential Vortex], Vol. 1 and 2, ISBN 3-9802-542-1-6 and ISBN 3-9802-542-2-4).

Since these potential vortices (electromagnetic longitudinal wave forms) permeate all kinds of shielding devices with virtually no loss, it is not surprising that all familiar kinds of technical shielding devices are ineffective. Since the beginning of the $20^{th}$ century, energy engineering has not made use of longitudinal waves, which spread potential waves. Nevertheless, the U.S. Pat. No. 513,138 (1897), U.S. Pat. No. 645,576 (1900) and U.S. Pat. No. 685,957 (1901) issued for Nikola TESLA should be mentioned here.

Potential vortices are emitted from the lateral wave field (transversal wave field) at open wire ends under voltage (open switches), during sudden voltage or current increases (e.g., inverter), during sudden discharges, around cathode ray tubes, e.g., in monitors, as well as during virtually all digital transmissions with the exception of light transmissions through optical cables, such as glass fiber cables with total reflection.

DE 198 50 238 A1 [is] apparently an apparatus for minimizing electromagnetic emissions of technical emitters which uses a closed induction loop in the shape of a Möbius winding to absorb potential vortices or transform them into lateral waves, respectively. This apparatus, however, is limited to the frequency range which is predetermined by the inherent inductance of the Möbius winding.

The task of the invention described herein is to offer an apparatus and a method to effectively minimize electromagnetic emissions of technical emitters.

SUMMARY OF THE INVENTION

This task is achieved by a single conductor which can be arranged at an emitter, an apparatus for transforming electromagnetic longitudinal waves into electromagnetic lateral waves, and an apparatus for transforming electromagnetic longitudinal waves into lateral waves, whereby the single conductor is electrically connected via the apparatus for transforming electromagnetic longitudinal waves with the apparatus for transforming electromagnetic lateral waves. Further advantageous variations of the apparatus according to the invention include a p-n transition that is electrically connected with the single conductor on the p range side and with the apparatus for transforming electromagnetic lateral waves on the n range side. The p-n transition can be a Zener diode and the apparatus for transforming electromagnetic lateral waves can be a resistor. The single conductor can be connected with a housing of the emitter, can be grounded, can be placed around the emitter in bifilar windings, and can be arranged at several emitters in serial arrangement. The apparatus can take the form of a circular serial electrical circuit of four diodes connected at a connection point to the single conductor. A resistor is placed between the second and third diode in the series from the connection point while a capacitor and a surge protector are arranged parallel to each other between the connection wire connecting the first and the second diode and the connection wire connecting the third and the fourth diode. The surge protector can take the form of a varistor or a Zener diode.

Different from the method and apparatus used in DE 198 50 238 A1, the method and apparatus according to the invention use the tendency of free vortices to wrap around an open response-enabled single-conductor (similar to the above mentioned US patents) and take advantage of the fact that potential vortices collapse, for example, in the depletion zone of a p-n transition into lateral wave forms making it possible to transfer them through familiar double-conductor systems in a closed wire as a direct current, e.g., via resistors as thermal energy.

Thus, the method and the apparatus according to the invention make use of the fact that potential vortices of technical origins characteristically center around threads with field response. These threads can be thin wires with a resting current or can be made from ferromagnetic material, as described in the above mentioned US patents. The interactions of technical devices discharging potential vortices are defined by similar conditions. The alternating sine-shaped current in the lateral wave range (Maxwell's equations), as supplied by power companies to residential users, represents only one technically measurable portion. The other part always derives from the longitudinal wave portion and occurs as a discharge of potential vortices. This can always and without exception be observed at the consumer end. In addition to constructional changes which attempt to prevent the discharge of potential vortices already at the source, the method and apparatus according to the invention can achieve a further minimization of already existing potential vortices and can reduce their discharge into the environment.

The invention calls for an apparatus in which a single-conductor placed at the emitter is connected with an.apparatus for transforming electromagnetic longitudinal waves into electromagnetic lateral waves which ideally offers a p-n transition in the p range. The n range of the p-n transition is electrically connected to an apparatus for transforming electromagnetic lateral waves. This can be a resistor which transforms the lateral waves in the familiar way indicated by Maxwell's equations into thermal energy.

It offers advantages to use a Zener diode for the p-n transition. The single-conductor is to be connected with the housing of the emitter if such housing is made from metal or is grounded. The single-conductor can also be grounded. In order to avoid inherent inductance in the familiar patterns, the emitter should loop around the single-conductor in bifilar windings.

The following section will describe a few examples of the apparatus and method according to the invention.

DESCRIPTION OF PREFERRED EMBODIMENTS

Figure 1:
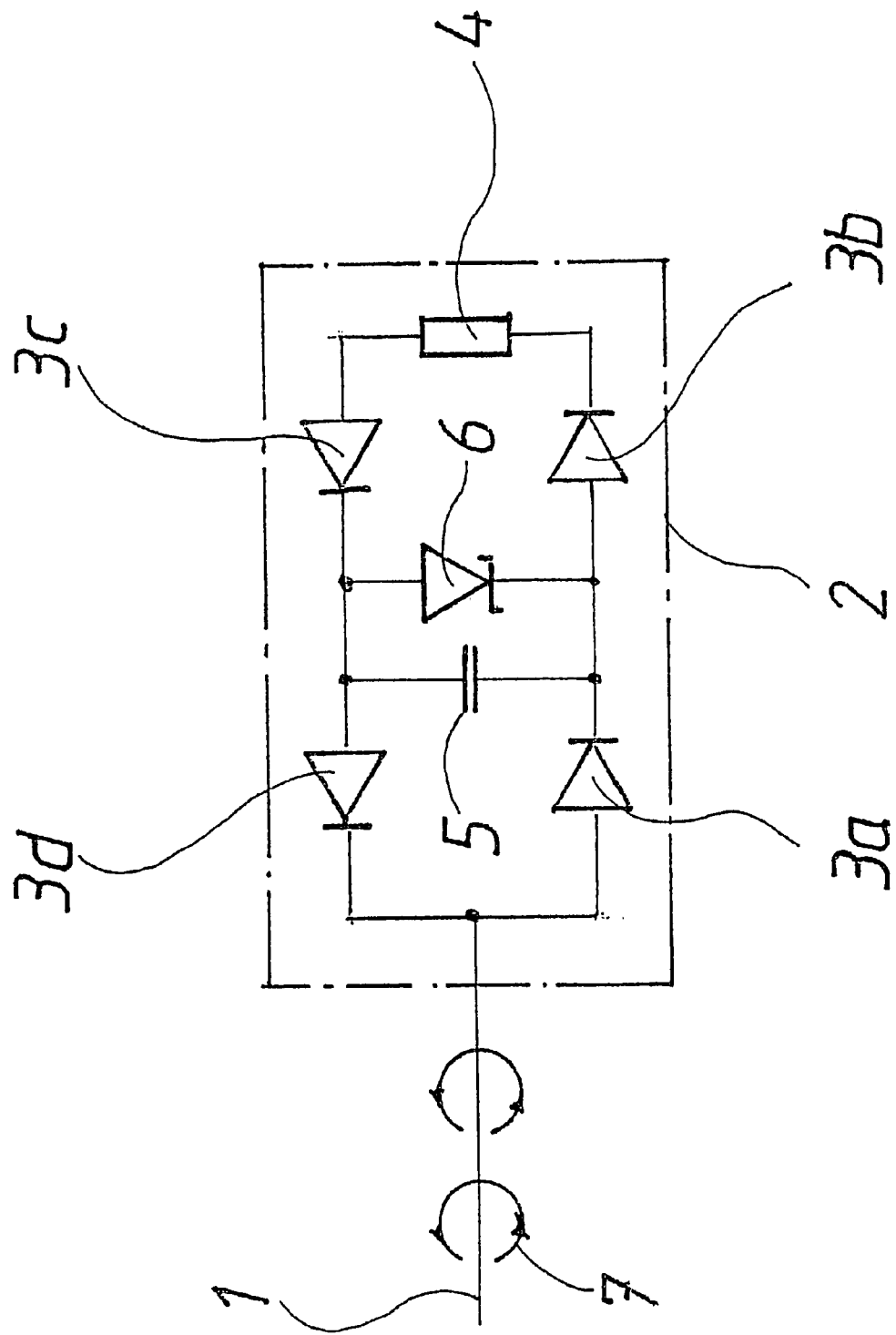
FIG. 1 an apparatus according to the invention

FIG. 1 shows an example of the basic arrangement for an apparatus according to the invention.

A ring vortex absorber 1 (response-enabled thread/single-conductor) carries longitudinal waves (ring vortices 7) to a serially arranged pair of diodes 3a and 3b. The potential vortices collapse at this pair of diodes. The arriving longitudinal wave frequency at the diodes can be measured with an oscilloscope. It becomes obvious that this frequency mostly consists of regular power line frequency over which higher frequencies are superimposed ("riding"). The energy content of the collapsed potential vortices is present at the capacitor 5 according to $W=U^2 \cdot C/2$ and at the resistor 4 according to $P=I^2 \cdot R$. This makes it possible to evaluate the effectiveness of the apparatus.

The diodes 3a and 3b are connected in series with the resistor 4 to which two additional diodes 3c and 3d are connected which, in turn, are connected in a ring circuit with the ring vortex absorber 1. Besides the already mentioned capacitor 5, a surge protector 6 (e.g., a Zener diode or a varistor) is placed, parallel to the capacitor, between the wire connecting the diodes 3a and 3b and the wire connecting the diodes 3c and 3d. This arrangement results in a lateral wave transformer 2 which transforms the ring vortices 7 captured from the single-conductor 1 into lateral waves in the depletion zone of the p-n transitions of the diodes.

Figure 2:
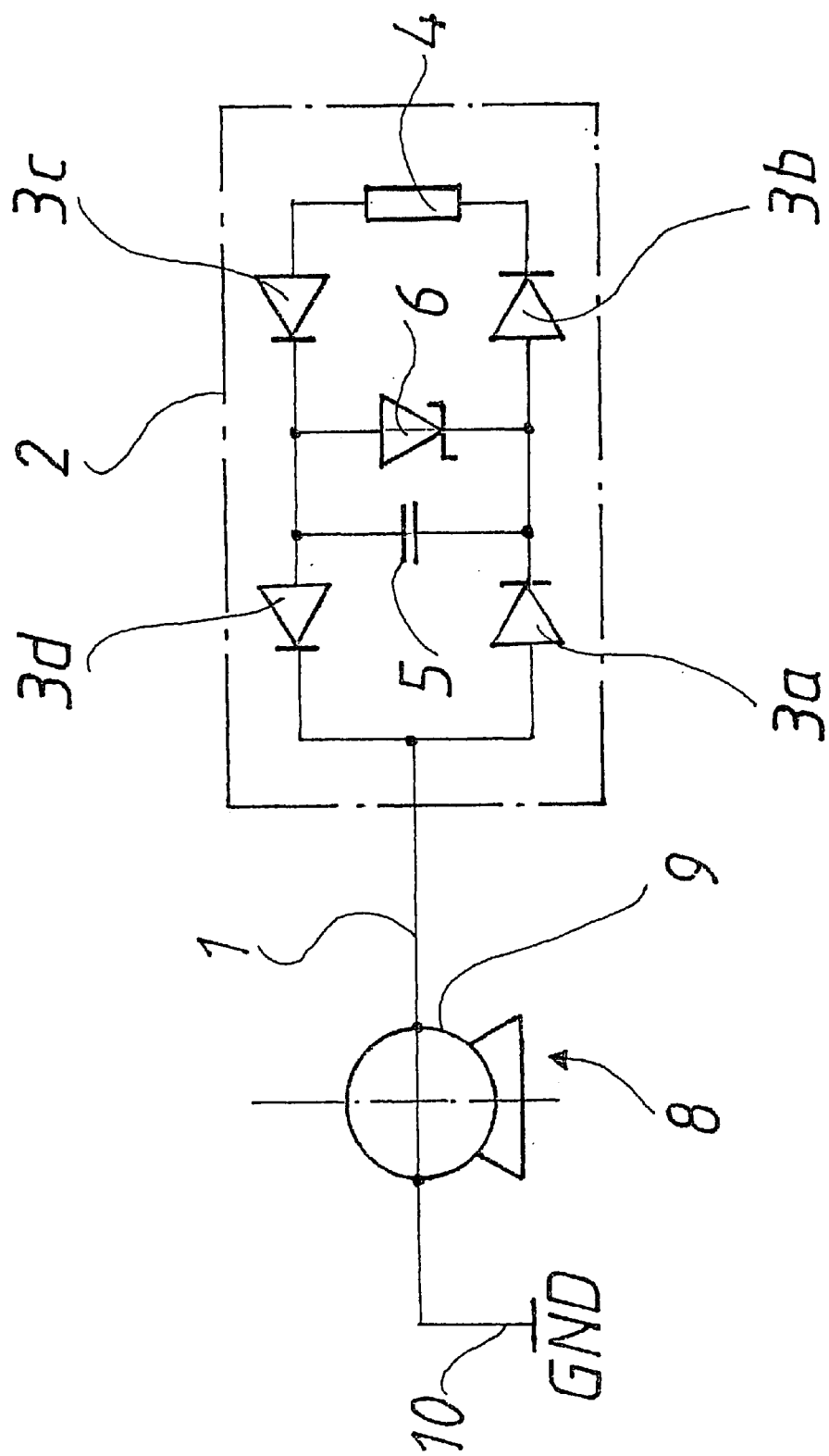
FIG. 2 another apparatus according to the invention

FIG. 2 shows another apparatus according to the invention. In this as in the following figures, the same references are used for identical elements and the descriptions for these elements are omitted.

As shown in FIG. 2, the effectiveness of the absorbing apparatus according to the invention is increased if—before the discharge of ring vortices—the longitudinal wave field at the housing 9—preferably grounded—of an emitter is part of the single-conductor. In this as in the following figures, grounding potential is indicated as GND and referenced as 10.

Figure 3:
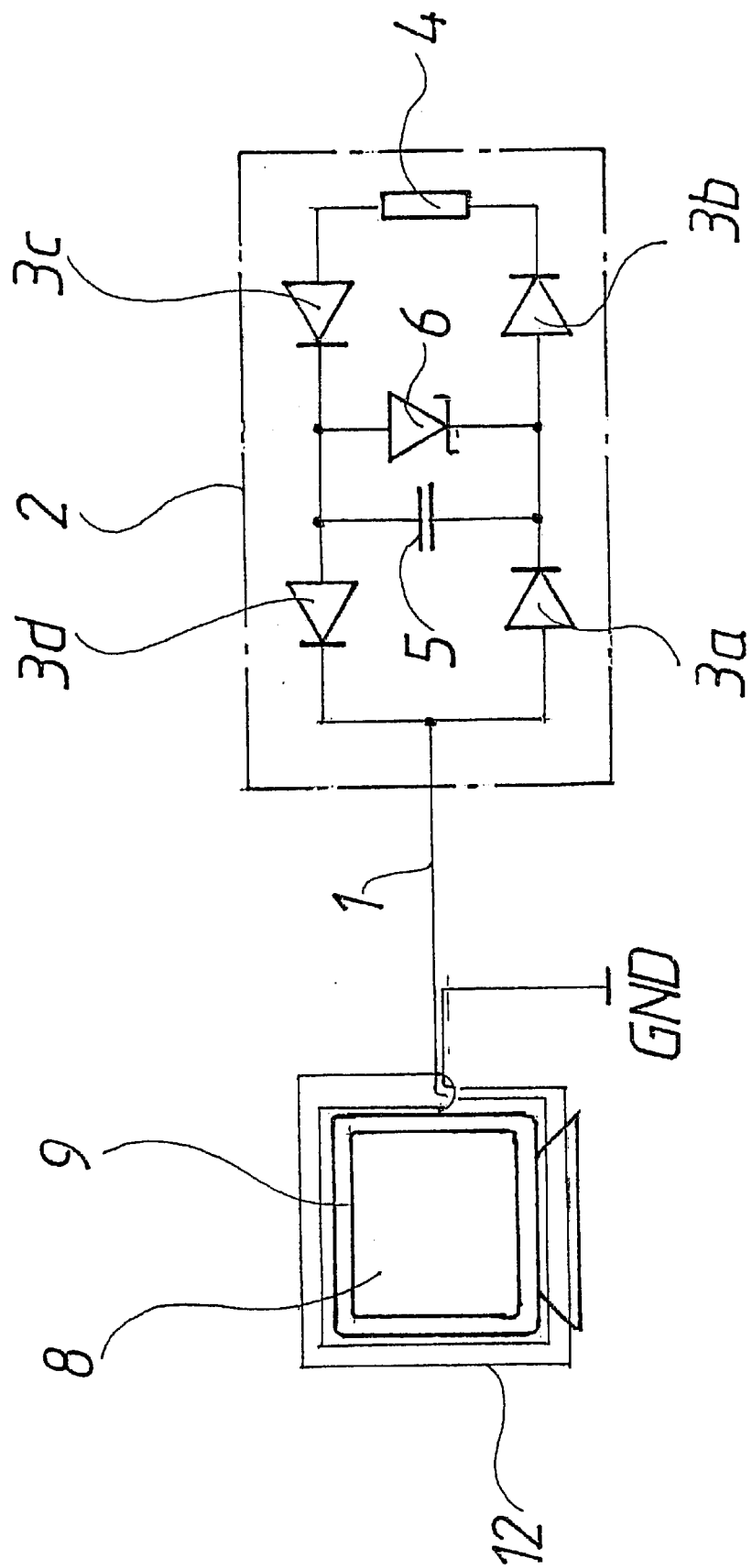
FIG. 3 an apparatus according to the invention

FIG. 3 shows another apparatus in which the housing 9 of an emitter 8 is made from non-conductive material. In this case, the absorbing single-conductor 1 is wrapped around the housing 9 in a bifilar loop 12. Wrapping the single-conductor 1 as a bifilar winding around the housing helps to avoid the inherent inductance which limits the frequency. The single-conductor 1 can thus accept any frequency since the bifilar winding is independent of inductance.

Figure 4:
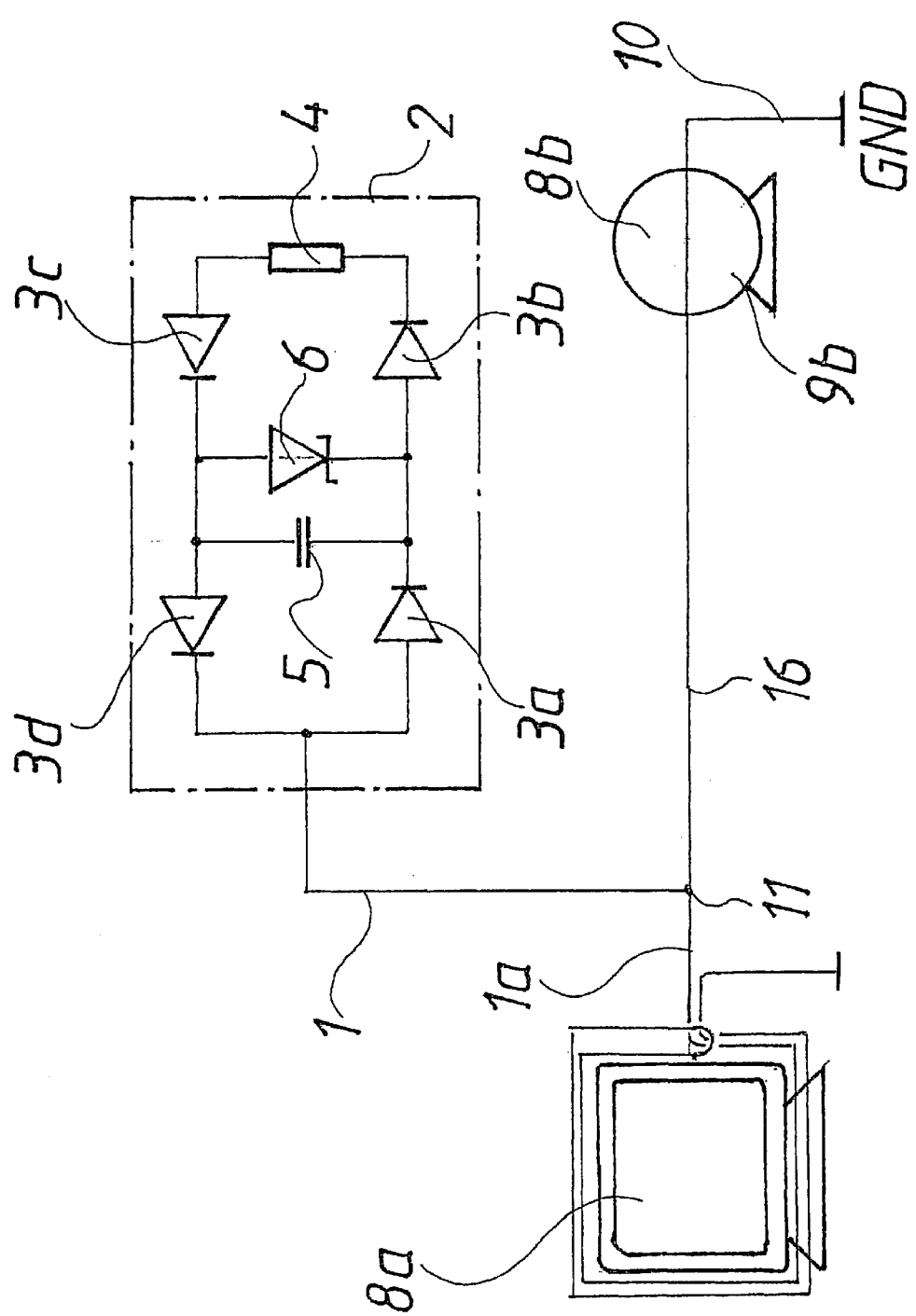
FIG. 4 an apparatus according to the invention.

FIG. 4 shows another apparatus according to the invention to which two different emitters 8a and 8b are connected. An absorber constructed according to the invention is capable of shielding several emitters in serial and parallel arrangements. FIG. 4 shows a variation of the apparatus in which a device 8a is connected with a single-conductor 1 via bifilar windings, and the housing 9b of a device 8b is connected to the ground 10, as well as to the single-conductor via wire 1b, whereby both single-conductors 1a and 1b from the devices 8a and 8b are connected with the main single-conductor 1 at the intersecting point 11. In this case, ring vortices from the single-conductors 1a and 1b disintegrate partially when they meet at the intersecting point 11. It should be noted that the single-conductor 1 does not necessarily have to be grounded.

Figure 5:
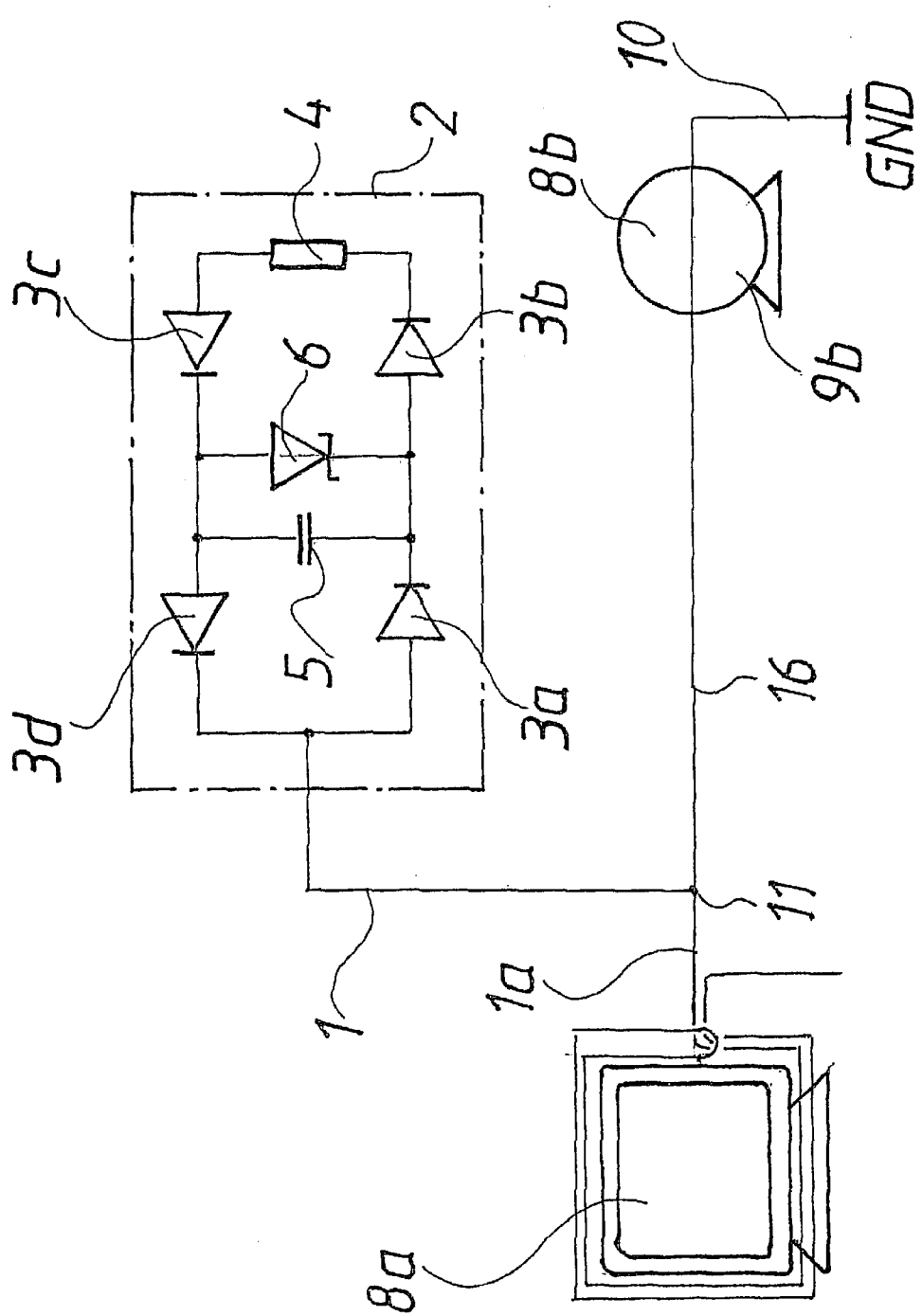
FIG. 5 an apparatus according to the invention

FIG. 5 shows another example which is similar to the example shown in FIG. 4. The only difference is that in this case the single-conductor 1b is connected to the ground 10 via the housing 9b of the device 8b.

The following summary can be offered: The method uses an apparatus for absorbing discharged ring vortices or longitudinal waves in combination with a lateral wave transformer. These elements are arranged as described above so that relevant longitudinal waves, via single-conductor technology, are passed on to a lateral wave transformer in which the longitudinally advancing potential vortices are transformed at the p-n transitions of semi-conductors (preferably diodes) into direct currents and then transformed, e.g., via resistors, into thermal energy.

What is claimed is:

1. Apparatus for minimizing electromagnetic emissions of technical emitters comprising:

a single conductor which can be connected to an emitter for absorbing electromagnetic longitudinal waves produced by the emitter, first apparatus coupled to the single conductor for transforming electromagnetic longitudinal waves into electromagnetic lateral waves, and second apparatus electrically connected to the first apparatus for depleting the electromagnetic lateral waves.

2. Apparatus according to claim 1 wherein the first apparatus has a p-n junction which is electrically connected to the single conductor on the p side and to the second apparatus on the n side.

3. Apparatus according to claim 2 wherein the p-n junction is a Zener diode.

4. Apparatus according to claim 1 wherein the second apparatus is a resistor.

5. Apparatus according to claim 1 wherein the single conductor is connected to a housing of the emitter.

6. Apparatus according to claim 1 wherein the single conductor is grounded.

7. Apparatus according to claim 1 wherein the single conductor is placed around the emitter in bifilar windings.

8. Apparatus according to claim 1 wherein the single conductor is connected to several emitters in serial arrangement.

9. Apparatus according to any of claims 1 or 5–8 wherein the single-conductor is connected at a connection point with a circular serial electrical circuit of four diodes, a resistor is placed between the second and third diode in the serial electrical circuit from the connection point, and a capacitor and a surge protector are arranged parallel to each other between a first connection wire connecting the first and the second diode and a second connection wire connecting the third and the fourth diode.

10. Apparatus according to claim 9 wherein the surge protector is one of the group consisting of a varistor or a Zener diode.

11. Apparatus for minimizing electromagnetic emissions of technical emitters comprising:

a single conductor connectable to an emitter for absorbing electromagnetic longitudinal waves produced by the emitter, a p-n junction which is electrically connected to the single conductor on the p side for transforming electromagnetic longitudinal waves into electromagnetic lateral waves, and a resistor coupled to the p-n junction on the n side for depleting the electromagnetic lateral waves.

12. The apparatus of claim 11 wherein the p-n junction comprises a plurality of p-n junctions arranged in a serial loop circuit that includes the resistor, the single conductor being coupled to the serial loop circuit at a connection point separated from the resistor by at least one p-n junction.

13. The apparatus of claim 12 wherein two p-n junctions are included in the serial loop circuit between the connection point for the single conductor and each end of the resistor.

14. The apparatus of claim 13 wherein a capacitor and a surge protector are arranged in parallel to each other between the two p-n junctions on one end of the resistor and the two p-n junctions on the other end of the resistor.

15. The apparatus of claim 14 wherein the surge protector comprises a varistor.

16. The apparatus of claim 14 wherein the surge protector comprises a Zener diode.

17. The apparatus of any of claims 11–16 wherein the wherein the single-conductor is connected to a housing of the emitter.

18. The apparatus of any of claims 11–16 wherein the single conductor is grounded.

19. The apparatus of any of claims 11–16 wherein the single conductor is placed around the emitter in bifilar windings.

20. The apparatus of any of claims 11–16 wherein the single conductor is connected to several emitters in serial arrangement.

21. A method for minimizing electromagnetic emissions of technical emitters comprising the steps of:
   connecting a single conductor to a p-n junction to transform electromagnetic longitudinal waves into electromagnetic lateral waves,
   connecting a resistor to a side of the p-n junction opposite the single conductor to deplete any electromagnetic lateral waves transformed by the p-n junction, and
   locating the single conductor in operable proximity to the technical emitter to absorb an electromagnetic longitudinal waves emitted by the technical emitter.

22. The method of claim 21 wherein the locating step comprises connecting the single conductor to a housing of the emitter.

23. The method of claim 21 wherein the locating step comprises placing the single conductor around the emitter in bifilar windings.

24. The method of any of claims 21–23 further comprising the step of grounding the single conductor.

25. The method of claim 24, wherein the locating step comprises connecting the single conductor to several emitters in serial arrangement.

* * * * *